(12) United States Patent
Gaster

(10) Patent No.: US 7,285,111 B2
(45) Date of Patent: Oct. 23, 2007

(54) APPARATUS AND METHODS FOR TRANSPORTABLE MEDICAL FLUID ADMINISTRATION

(76) Inventor: Michelle Gaster, 13460 Firth Dr., Beverly Hills, CA (US) 90210

( * ) Notice: Subject to any disclaimer, the term of this patent is extended or adjusted under 35 U.S.C. 154(b) by 418 days.

(21) Appl. No.: 10/642,854

(22) Filed: Aug. 18, 2003

(65) Prior Publication Data

US 2005/0040126 A1 Feb. 24, 2005

(51) Int. Cl.
*A61M 37/00* (2006.01)
(52) U.S. Cl. .................. 604/131; 604/19; 604/48; 604/93.01
(58) Field of Classification Search ............... 24/134; 248/125, 289.1, 12, 230.1; 5/508; 604/131, 604/19, 48, 93.01
See application file for complete search history.

(56) References Cited

U.S. PATENT DOCUMENTS

| | | | | |
|---|---|---|---|---|
| 4,106,165 A | 8/1978 | Clowers et al. | ............... | 24/134 |
| 4,114,273 A | * 9/1978 | McGaha | ..................... | 433/27 |
| D252,300 S | 7/1979 | Pryor | ........................... | D6/28 |
| 4,807,837 A | * 2/1989 | Gawlik et al. | ........... | 248/125.8 |
| 4,832,294 A | * 5/1989 | Eidem | ..................... | 248/125.8 |
| 4,886,237 A | 12/1989 | Dennis | ..................... | 248/289.1 |
| 4,905,944 A | 3/1990 | Jost et al. | .................... | 248/125 |
| 4,945,592 A | 8/1990 | Sims et al. | ..................... | 5/508 |
| 4,971,205 A | 11/1990 | Hopkins | ....................... | 211/13 |
| 5,054,732 A | 10/1991 | Sukup | ..................... | 248/309.1 |
| 5,135,191 A | 8/1992 | Schmuhl | ..................... | 248/125 |
| 5,222,946 A | 6/1993 | Kamen | ........................ | 604/151 |
| 5,458,305 A | 10/1995 | Woodward | .................. | 248/121 |
| 5,494,446 A | 2/1996 | DeLucia et al. | .............. | 439/4 |
| 5,645,147 A | 7/1997 | Kovacik et al. | ........... | 191/12.2 |
| 5,700,257 A | 12/1997 | Minick et al. | .............. | 604/408 |
| 5,823,503 A | 10/1998 | Wasserman | ................. | 248/683 |
| 5,928,200 A | 7/1999 | Thorne et al. | .............. | 604/195 |
| 6,109,572 A | 8/2000 | Urban et al. | ................ | 248/159 |
| 6,241,630 B1 | 6/2001 | Alberti | ........................ | 473/492 |
| 6,293,485 B1 | 9/2001 | Hollowed | ................ | 242/385.3 |
| 6,343,568 B1 | 2/2002 | McClasky | .................... | 119/248 |
| 6,349,808 B1 | 2/2002 | Bryant | ....................... | 191/12.2 |
| 6,409,131 B1 | 6/2002 | Bentley et al. | .......... | 248/219.4 |

* cited by examiner

*Primary Examiner*—Kevin C. Sirmons
*Assistant Examiner*—Phillip Gray
(74) *Attorney, Agent, or Firm*—Khorsandi Patent Law Group, A Law Corporation; Marilyn R. Khorsandi

(57) ABSTRACT

The exemplary embodiment of the present invention would provide an apparatus for concealed transport of a medical fluid administration device. The medical fluid administration device would be capable of infusing medical fluids to, or collecting medical fluids from, as the case may be, the body of a patient during concealed transport. The exemplary apparatus would comprise one or more of the following: a stand disposed within a carrying case, said stand capable of being extended during stationary use or collapsed during ambulatory use; a medical fluid pump disposed within the carrying case, said pump capable of delivering or collecting medical fluids during concealed transport within the carrying case; and a tubing retraction device for engaging tubing for delivery of medical fluids to, or collection of medical fluids from, a body of a patient.

18 Claims, 6 Drawing Sheets

APPARATUS AND METHODS FOR TRANSPORTABLE MEDICAL FLUID ADMINISTRATION

FIELD OF THE INVENTION

The field of the present invention is medical apparatus and methods for medical fluid delivery and collection, and more particularly, personally transportable medical fluid delivery and collection administration apparatus and methods.

BACKGROUND OF THE INVENTION

Various types of medication or other fluids can be infused into a patient's body using intravenous ("IV") or other fluid delivery apparatus. In addition, various types of fluids can be collected from a patient's body such as, for example, urine through a catheter.

Administering fluid delivery to a patient has often involved the use of flexible containers of fluid suspended on a vertically displaced pole, sometimes with a fluid pump, and often mounted on a stand. Such medical fluid deliver apparatus configurations limit the mobility of otherwise ambulatory patients.

Administering medical body fluid collection has often involved securing a collection bag to a person's body inside a person's clothing. Such medical body fluid collection apparatus configurations may be bulky, uncomfortable or unpleasant for the patient.

A better way of administering medical fluid delivery and collection is needed.

SUMMARY OF THE INVENTION

The present invention provides a medical fluid administration device for delivering, such as intravenously, or collecting, medical fluids while the device is in either a collapsed concealed state or in an expanded unconcealed state.

The present invention provides a portable apparatus for collecting medical body fluids from a patient while the apparatus is in either a collapsed concealed state or in an expanded unconcealed state.

The present invention provides a medical support system for administering the delivery of medical fluids to a patient, or the collecting of medical body fluids from a patient, as the case may be, that comprises a portable telescoping stand and a tube winding/retraction device that can be concealed inside a carrying case.

In the exemplary embodiment of the present invention, the carrying case would have two zippered compartments: one for personal storage for objects such as a wallet; the other for medical fluid delivery or collection, as the case may be, equipment. The compartment for medical fluid delivery or collection equipment, as the case may be, would hold a telescoping pole, a tube winding/retraction device, and would provide room for an extra fluid reservoir bag or other similarly sized equipment. In the exemplary embodiment, the telescoping pole would support a fluid reservoir bag and portable fluid regulation pump. The carrying case would provide an aperture in the side of the case to allow the tubing to exit the case while the zipper to the compartment containing the tubing is closed.

The patient may walk around with, or transport the exemplary carrying case with the pole and equipment concealed inside and at the same time receive, or deliver, as the case may be, the relevant medical fluids. If the patient is stationary for a while, the patient may open the compartment containing the tubing and raise the telescoping pole so as to aid the pump in transmitting the fluids from or to, as the case may be, the fluid reservoir bag.

The exemplary embodiment of the present invention comprises a telescoping pole comprising a means for suspending a medical fluid container, and a tubing retraction device for engaging tubing for delivery, or collection, of medical fluids to or from a patient.

The exemplary embodiment of the present invention further comprises a carrying case, said carrying case comprising a compartment for holding the telescoping pole, said carrying case further comprising an aperture through which fluid delivery tubing can be inserted.

In the exemplary embodiment of the present invention, the carrying case compartment comprises a floor, the telescoping pole comprises a base, and the base of the telescoping pole is mounted on the floor of the carrying case compartment.

In the exemplary embodiment of the present invention, the telescoping pole is spring loaded.

In the exemplary embodiment of the present invention, the telescoping pole comprises a base sub-pole, a top sub-pole, and a plurality of telescoping sub-poles, the base sub-pole comprising an aperture, each telescoping sub-pole comprising a spring-loaded button and an aperture, the top sub-pole comprising a spring-loaded button.

In the exemplary embodiment of the present invention, the telescoping pole comprises a top, and further comprises a means for suspending the medical fluid container from the top of the telescoping pole.

The exemplary embodiment of the present invention further comprises a means for suspending a portable fluid pump.

An alternative exemplary embodiment of the present invention comprises a plurality of telescoping poles mounted to an exterior bottom of a carrying case, a stationary pole mounted to an interior floor of the carrying case, said stationary pole comprising a means for suspending a medical fluid container, and a tubing retraction device for engaging tubing for medical delivery or collection of fluids.

The exemplary embodiment of the present invention would provide an apparatus for concealed transport of a medical fluid administration device. The medical fluid administration device would be capable of infusing medical fluids to, or collecting medical fluids from, as the case may be, the body of a patient during concealed transport. The exemplary apparatus would comprise one or more of the following: a stand disposed within a carrying case, said stand capable of being extended during stationary use or collapsed during ambulatory use; a medical fluid pump disposed within the carrying case, said pump capable of delivering or collecting medical fluids during concealed transport within the carrying case; and a tubing retraction device for engaging tubing for delivery of medical fluids to, or collection of medical fluids from, a body of a patient.

One exemplary embodiment of the present invention would provide an apparatus for concealed transport of a medical fluid administration device; the device would be capable of infusing medical fluids to, or collecting medical fluids from, the body of a patient during concealed transport; the apparatus would comprise: a stand disposed within a carrying case, said stand capable of being extended during stationary use or collapsed during ambulatory use; and a medical fluid pump disposed within the carrying case, said pump capable of delivering or collecting medical fluids during concealed transport within the carrying case.

In a further alternative exemplary embodiment of the present invention, an apparatus for concealed transport of a medical fluid administration device would be provided in which the device would be capable of infusing medical fluids to, or collecting medical fluids from, the body of a patient during concealed transport; the apparatus would comprise: a medical fluid pump disposed within a carrying case, said pump capable of delivering or collecting medical fluids during concealed transport within the carrying case; and a tubing retraction device for engaging tubing for delivery of medical fluids to, or collection of medical fluids from, a body of a patient.

BRIEF DESCRIPTION OF THE DRAWINGS

These and other features of the present invention are more fully set forth in the following description of non-limiting exemplary embodiments of the invention. The description is presented with reference to the accompanying drawings in which.

DETAILED DESCRIPTION OF THE INVENTION

Figure 1:
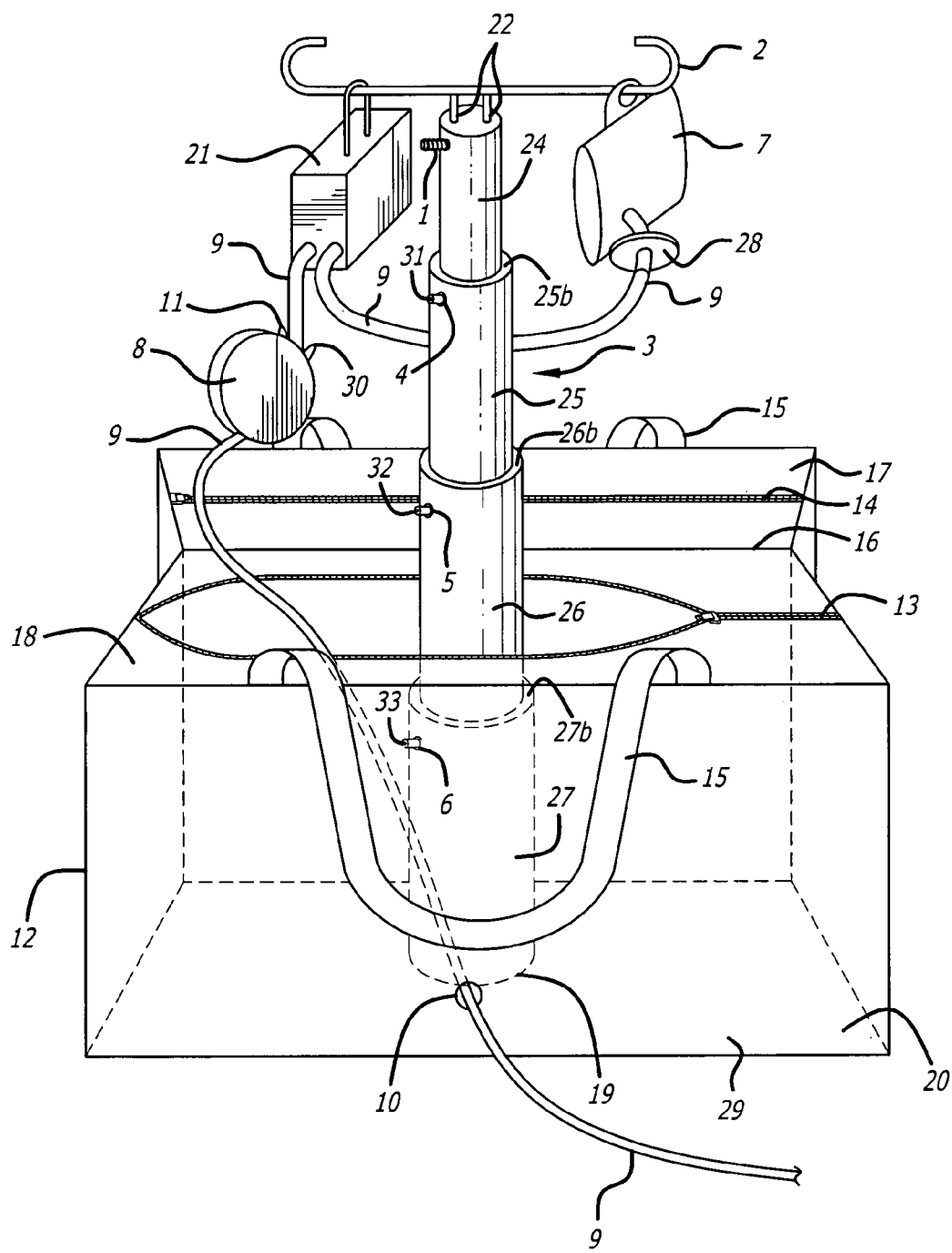
FIG. 1 is a perspective view of an exemplary carrying case with an exemplary telescoping pole in an extended state in an exemplary embodiment of the present invention.

FIG. 1 is a perspective view of an exemplary carrying case 12 with an exemplary telescoping pole 3 in an extended state in an exemplary embodiment of the present invention.

As depicted in FIG. 1, the exemplary embodiment of the present invention would provide a telescoping pole 3. In an alternative embodiment (not shown), a loop may be provided on the carrying case 12 to hang the case 12 if the use of the telescoping pole 3 is not desired.

As depicted in FIG. 1, the exemplary telescoping pole 3 of the exemplary embodiment of the present invention would comprise a plurality of tubular members, or pole segments, 24, 25, 26, and 27. In the exemplary embodiment, each of the tubular members 24, 25, 26, and 27 would be of equal length, and would each be approximately eight (8) inches long. When fully extended, the telescoping pole 3 of the exemplary embodiment would measure approximately two and one half (2½) feet in height. In the exemplary embodiment, the tubular members 24, 25, 26, and 27 would be made of a strong, lightweight plastic or aluminum material. As will be understood by someone with ordinary skill in the art, the materials, the number of tubular members and the actual and relative length of the tubular members, described herein, are exemplary and illustrative, and are not a limitation of the invention; variations in the materials used, the number of tubular members, and the actual and relative length of each tubular member are possible without departing from the spirit of the present invention.

As depicted in FIG. 1, the exemplary embodiment of the present invention would provide a base tubular member 27, a top telescoping tubular member 24, and two middle telescoping tubular members 25 and 26. The diameter of each telescoping tubular member 26, 25, and 24 would decrease in diameter from the preceding tubular member, 27, 26, and 25, respectively. Due to the decreasing diameter, each subsequent telescoping tubular member 26, 25, and 24, respectively, would fit inside the preceding tubular member 27, 26, and 25, respectively. In the exemplary embodiment, the diameter of the base pole 27 would be approximately 2 inches; the diameters of telescoping tubular members 26, 25, and 24 would each, respectively, decrease by one-half (½) inch.

Continuing with FIG. 1, in the exemplary embodiment, at the top of base tubular member 27, an aperture 6 would be provided; at the top of telescoping tubular member 26, an aperture 5 would be provided; at the bottom of telescoping tubular member 26 a spring-loaded locking button 33 would be provided; at the top of telescoping tubular member 25, an aperture 4 would be provided; at the bottom of telescoping tubular member 25, a spring-loaded locking button 32 would be provided; at the top of top telescoping tubular member 24, a spring-loaded locking button 1 would be provided; and at the bottom of top telescoping tubular member 24, a spring-loaded locking button 31 would be provided.

As depicted in FIG. 1, when the exemplary telescoping pole 3 of the exemplary embodiment of the present invention is fully extended, telescoping pole 3 would be secured in its extended position by locking buttons 31, 32 and 33. As depicted in FIG. 1, in the fully extended position of telescoping pole 3, spring loaded button 31 would extend through aperture 4 in telescoping member 25 to lock the top telescoping member 24 in the extended position. Similarly, spring loaded button 32 would lock telescoping tubular member 25 in the extended position by extending through aperture 5 of telescoping member 26; and spring loaded button 33 would lock telescoping member 26 in place by extending through aperture 6 of the base tubular member 27.

Figure 2:
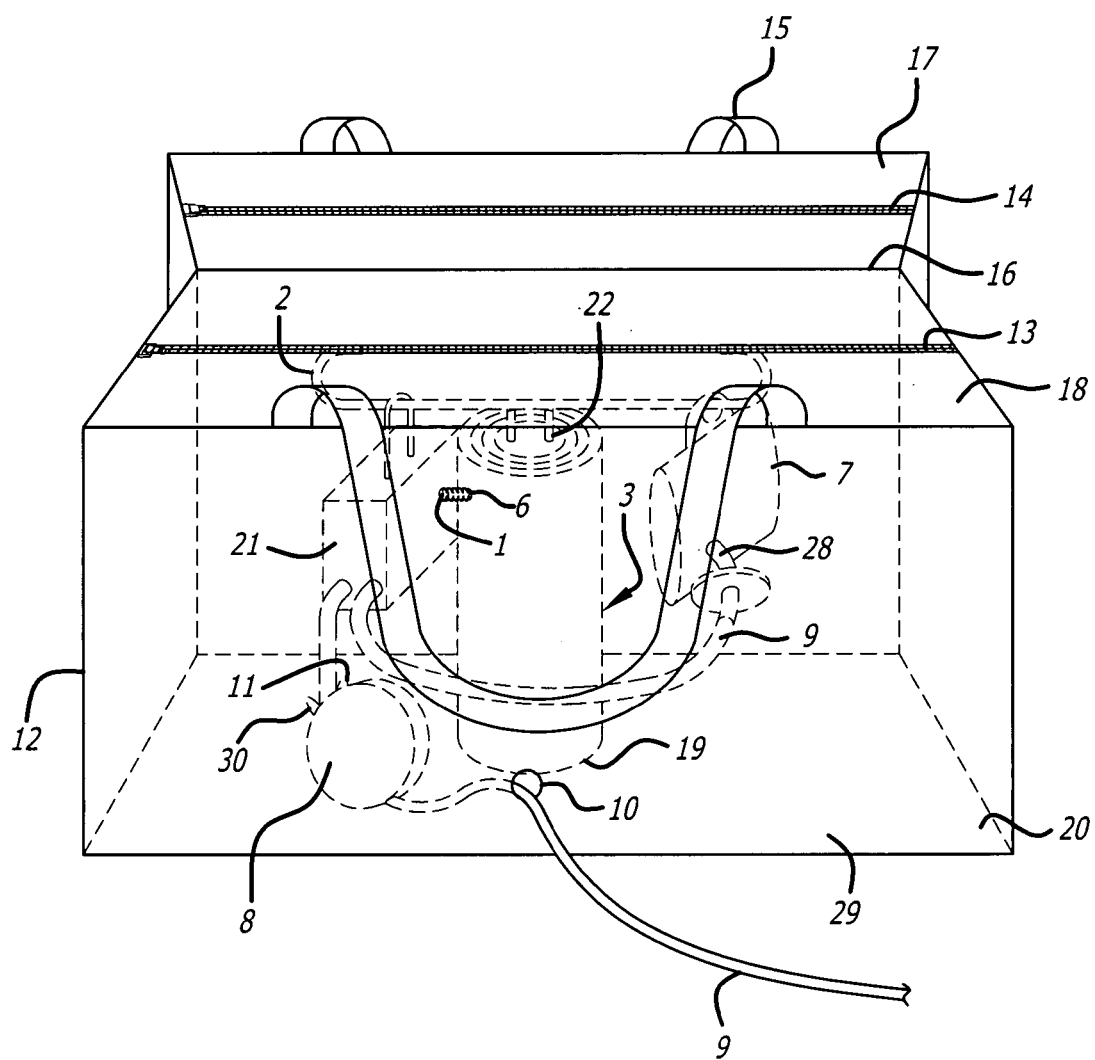
FIG. 2 is a perspective view of the exemplary carrying case with the exemplary telescoping pole in a fully collapsed state in an exemplary embodiment of the present invention.
Figure 3:
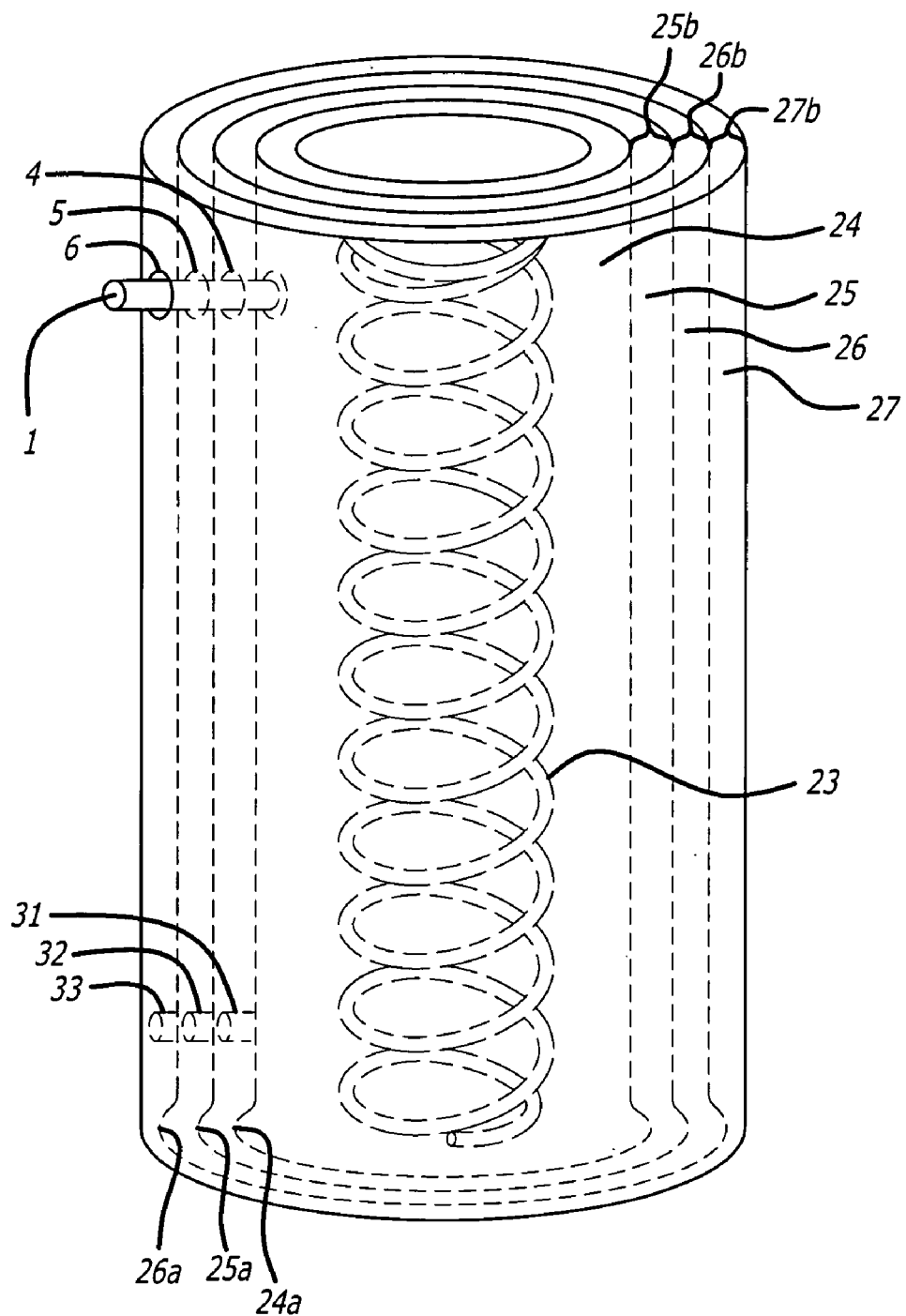
FIG. 3 is a side view depicting the exemplary telescoping pole in a fully collapsed state in an exemplary embodiment of the present invention.

FIG. 2 is a perspective view of the exemplary carrying case with the exemplary telescoping pole 3 in a fully collapsed state in an exemplary embodiment of the present invention. FIG. 3 is a side view depicting the exemplary telescoping pole 3 in a fully collapsed state in an exemplary embodiment of the present invention.

As depicted in FIGS. 2 and 3, when the exemplary telescoping pole 3 of the exemplary embodiment of the present invention is fully collapsed, spring-loaded button 1 would extend through apertures 4 (not visible in FIG. 2, but visible in FIG. 3), 5 (not visible in FIG. 2, but visible in FIG. 3) and 6 to lock the telescoping pole 3 in a fully collapsed state. Further, as depicted in FIG. 3, when the exemplary telescoping pole 3 of the exemplary embodiment of the present invention is fully collapsed, locking buttons 31, 32 and 33 would be compressed inside the tubular members 25, 26 and 27, respectively.

As depicted in FIG. 3, in the exemplary embodiment of the telescoping pole 3, each of the telescoping tubular members 24, 25 and 26 would provide an outwardly flared ridge, 24a, 25a, and 26a, respectively, at the bottom of the respective tubular member. As depicted in FIGS. 1 and 3, tubular members 25, 26 and 27 respectively would provide an inward detent 25b, 26b, and 27b, respectively. When the telescoping pole 3 is in its fully extended state such as depicted in FIG. 1, the outwardly flared ridges 24a, 25a, and 26a of the telescoping tubular members 24, 25 and 26 would be resisted by the inward detents of 25b, 26b, and 27b, respectively, of tubular members 25, 26 and 27, respectively, to prevent any telescoping tubular member 24, 25, 26 from becoming disengaged from the telescoping pole 3.

As depicted in e.g., FIG. 1, in the exemplary embodiment of the present invention, a carrying case 12 would be provided. As depicted in FIG. 1, the exemplary carrying case 12 would provide a center divider 16 which would separate a compartment 17 for holding personal items, such as a wallet and makeup, from a compartment 18 for holding fluid delivery/collection supplies, such as intravenous fluid delivery supplies, e.g., a bag 7 (such as an IV bag), tubing 9 (such as IV tubing), small pump 21 (such as an IV pump) and a tube winding/retraction device 8 (such as an IV tube winding/retraction device), as well as for holding the telescoping pole 3.

Bag 7 would contain fluid for delivery to a patient, or alternatively, would serve as a collection reservoir for fluids, such as, e.g., urine, collected from a patient. Tubing 9 would be coupled to bag 7 and would connect bag 7 to pump 21; more tubing 9 would be coupled to pump 21 to connect pump 21 to the patient (not shown). Tubing 9 would alternatively carry medical fluids from bag 7, through pump 21, for delivery to the patient (not shown); or alternatively, would carry medical body fluids from the patient (not shown) through pump 21, to the fluid collection bag 7. Pump 21 would pump fluid from bag 7 to be delivered, such as intravenously, to the patient, or alternatively, would pump fluid collected from the patient to fluid collection bag 7.

When the present invention is used as a medical body fluid collection system, tubing 9 could be made of opaque material to conceal the nature of the fluid being transported. Alternatively, an expandable sleeve (not shown) of opaque material could be provided to cover the expanse of tubing between the carrying case 12 and the patient (not shown). The expandable sleeve could be made of various types of cloth or plastic. An exemplary expandable sleeve would be made in a tubular form; one end would be connected to the exterior of aperture 10 (see, e.g., FIG. 1) on carrying case 12; the other end could be connected to the distal end of tubing 9 for connection to the patient via an intravenous needle or other patient connecting device, such as, for example, a catheter, depending on the application.

As described further below, tube winding/retraction device 8 would be provided to allow extension or retraction of tubing 9—when telescoping pole 3 is fully extended, and/or when the carry case 12 is placed in a stationary position, such as on the ground next to a patient in a chair, tube winding/retraction device 8 would be used to unwind (extend) the tubing 9; when telescoping pole is fully collapsed, such as when the patient is carrying the carrying case 12, tube winding/retraction device 8 would be used to wind (retract) the tubing so that as much of it as possible would be concealed inside the carrying case 12.

The exemplary embodiments of the invention herein generally depict and describe non-limiting intravenous fluid delivery embodiments. It will be understood by someone with ordinary skill in the art that the present invention is not limited to fluid delivery embodiments. Rather, the invention pertains equally to medical body fluid collection. Therefore, as will be understood by someone with ordinary skill in the art, non-limiting references herein to IV (and/or intravenous) tubing, pumps, and the like, will apply equally to other medical fluid delivery and medical body fluid collection applications. In medical body fluid collection embodiments, it will be understood by someone with ordinary skill in the art that the pump 21 would be configured to transport bodily fluids, for example, urine, from the patient to the collection bag 7—that is, the direction of the fluid will be reversed from the exemplary intravenous embodiments described herein; and bag 7 will be used as a collection reservoir as opposed to a delivery reservoir. Even though the direction of the flow of fluids will be reversed, the pump 21 will be used to regulate the flow of the fluids.

As will be understood by someone with ordinary skill in the art, medical fluid delivery or collection systems use pumps to regulate the flow of delivery, or collection, as the case may be, of the particular medical fluid—that is, the flow of the delivery or collection of the fluid is regulated by the pump 21 regardless of the position of the fluid delivery (or collection) bag 7. It will be understood by someone with ordinary skill in the art that, depending on the height of the collection bag 7 in relation to the point at which the fluid is delivered into, or out of, as the case may be, a patient, it may be possible to turn the pump 21 off and allow gravity to deliver or collect the fluid, as the case may be. However, it would not be a requirement with the present invention that the pump 21 be turned off when the telescoping pole 3 is expanded. Rather, the pump 21 may be left on in order to ensure proper flow regulation.

In the exemplary embodiment, compartment 17 would open and close by means of zipper 14. Compartment 18 would open and close by means of zipper 13. As will be understood by someone with ordinary skill in the art, use of zippers 13 and 14 in the exemplary embodiment is not a limitation of the invention. Other closure means could be used without departing form the spirit of the invention. Further, as someone with ordinary skill in the art will understand, alternative carrying case construction could be provided without departing from the spirit of the invention. For example, an alternative carrying case could provide a single compartment, e.g., compartment 18; compartment 18 could be provided with a C-shaped zippered flap. Other carrying case configurations are possible. For example, a divider 16' (not shown) could be provided that was not centrally located in the case 12. Further, the carrying case 12 could be configured in the form of a purse, a backpack, briefcase, or other types of utilitarian or fashion carrying case forms not typically associated with hospitals or sick rooms.

Equivalently, the carrying case 12 could provide a pump 21 for other than intravenous fluid delivery, including, but not limited to, various medical fluid delivery and collection systems such as, for example, gastrointestinal nourishment delivery, insulin delivery, urine collection (such as through a catheter), and colostomy fluid collection.

In the exemplary embodiment of the present invention, the center divider 16 of the carrying case 12 would be made of a cloth stretched across the center of the carrying case 12 separating the personal carrying compartment 17 from the compartment 18 containing IV equipment. In the exemplary embodiment, the sides of the carrying case 12 would be made of cardboard covered in a strong, durable, stiff fabric. In the exemplary embodiment, handles 15 would be provided. In the exemplary embodiment, the handles 15 would be made of a strong fabric. The zippers 14 and 13 of compartments 17 and 18, respectively, could be closed for privacy and to prevent things from spilling out of the carrying case 12.

Continuing with FIG. 1, compartment 18 would provide a bottom 20. In the exemplary embodiment, the bottom 20 would comprise a large plastic board and would measure approximately 10 inches by 6 inches.

As depicted in FIG. 1, in the exemplary embodiment, the base tubular member 27 would be attached to the bottom 20 of carrying case 12 at location 19 which is approximately the center of the bottom 20.

As depicted in FIG. 1, in the exemplary embodiment, a double-sided "J" shaped hook 2 would be provided. In the exemplary embodiment, the double-sided "J" shaped hook 2 would be made of a strong metal with a length of approximately 4 inches and would be affixed to the top of the top telescoping tubular member 24 by means of two vertical posts 22.

As depicted in FIG. 1, in the exemplary embodiment, a tube-winding/retraction device 8 would be provided. In the exemplary embodiment, the tube-winding device 8 would measure approximately 4 inches in diameter and approximately 1 inch wide. In the exemplary embodiment, thick-walled, relatively large diameter tubing 9 would be provided for use with the tube-winding device 8. Thick-walled, relatively large diameter tubing 9 would tend to not dent, be crushed, or deform substantially, when wound into, and around the core of, the tube-winding/retraction device 8. Therefore, by using thick-walled, relatively large diameter tubing 9, constant flow of the fluid to be delivered intravenously would be delivered without obstruction. It will be understood by someone with ordinary skill in the art that the internal diameter of the tubing 9 will need to be appropriate relative to the fluid regulation pump 21 and the fluid for the particular application. The exemplary tube-winding/retraction device 8 of the exemplary embodiment would use a friction locking mechanism with which to lock the retracted or extended tubing 9 in place. Other tube-winding/retraction device configurations could be used, including, for example, a spool (not shown) upon which the tubing 9 could be wound.

Tube-winding/retraction device 8 would be provided to allow a patient to adjust the length of IV tube 9. In the exemplary embodiment, a locking button 11 and a release button 30 would be provided on the tube-winding/retraction device 8. Pressing locking button 11 on tube-winding/retraction device 8 would lock IV tube 9 at a desired length by griping the tube 9, but not obstructing the flow of fluid through the tube 9. Pressing release button 30 would release locking button 11 so that the IV tube 9 can be lengthened or shortened and then locked again so that there is no tension pulling on IV tube 9. Providing tube-winding/retraction device 8 would allow a patient to adjust the length of the IV tubing 9 to suit the patient's needs. For example, the IV tubing 9 could be retracted to a short length when the patient is carrying the carrying case 12 with the telescoping pole 3 in a collapsed state, such as is depicted, e.g., in FIG. 2. When the patient is sitting with, e.g., the carrying case 12 on the ground and extends telescoping pole 3, the patient would release the locking button 11 by pressing release button 30 so that the IV tubing 9 could be extended.

Figure 4:
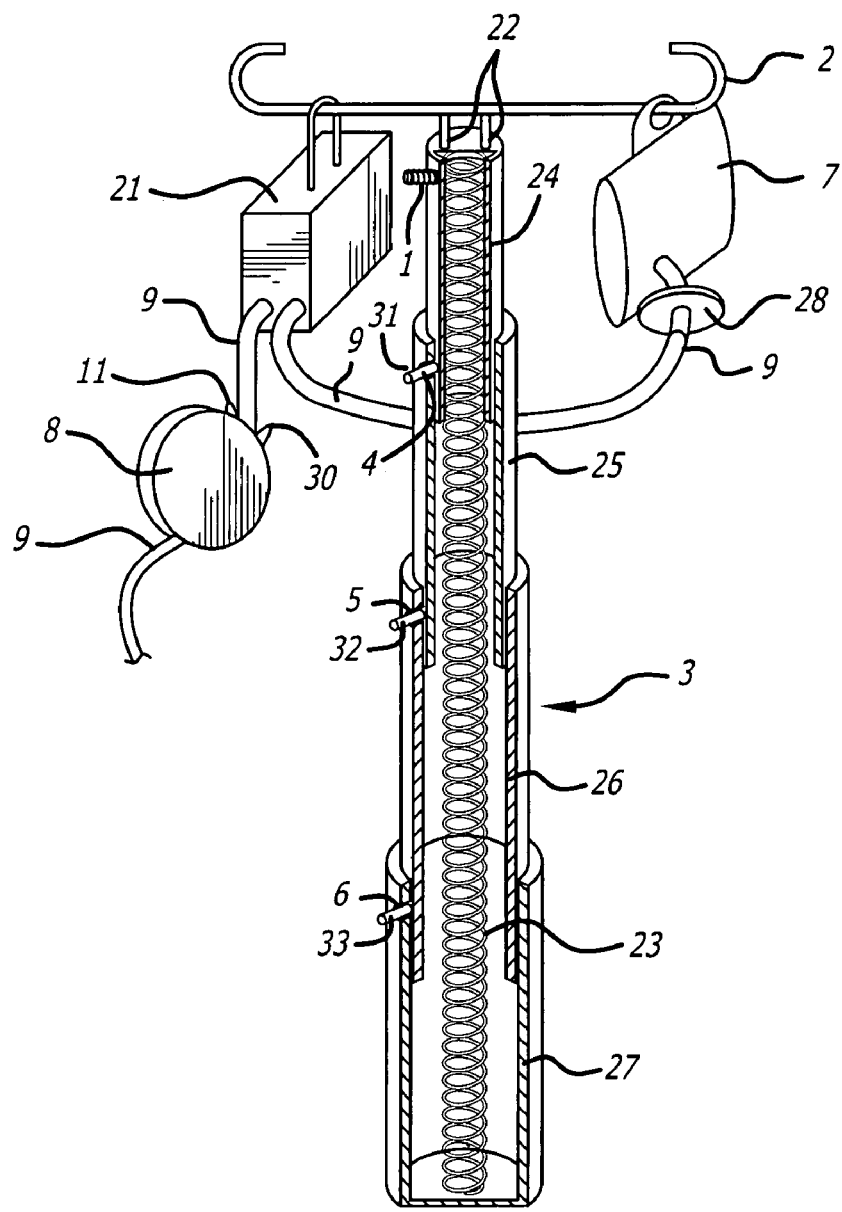
FIG. 4 is a vertical cross section of the exemplary telescoping pole in an exemplary embodiment of the present invention.

FIG. 4 is a vertical cross section of the exemplary telescoping pole 3 in the exemplary embodiment of the present invention. As depicted in FIGS. 3 and 4, the exemplary telescoping pole 3 would be spring loaded with spring 23. In the exemplary embodiment, telescoping pole 3 would be held in a fully collapsed position, and as depicted in FIG. 3, the spring 23 would be held in a fully compressed position, by spring-loaded button 1 extending through apertures 4, 5, and 6.

Returning to FIG. 1, in the exemplary embodiment, an aperture 10 would be provided in side 29 of carrying case 12. In the exemplary embodiment, aperture 10 would be approximately ¾ inch in diameter. IV tubing 9 would be inserted through aperture 10 from inside compartment 18 to the patient.

In the exemplary embodiment, the carrying case 12 would weigh approximately five (5) pounds when loaded with all of the IV equipment, including a small pump 21, needed to intravenously deliver fluids. Such an apparatus would provide a convenient, lightweight fluid delivery system for the patient. The personal compartment 17 of the exemplary embodiment would provide storage for personal items thereby reducing the need for the patient to carry additional bags. The exemplary embodiment of the present invention would thus provide portable, compact, disguised and convenient intravenous fluid delivery for highly mobile patients receiving IV fluids who wish to engage in everyday activities.

In order to administer fluid delivery, the IV bag 7 would be hung from one side of the double-sided "J"-shaped hook 2 which is attached to the telescoping pole 3. The IV tube 9 would be attached to IV bag 7 at nozzle 28. The IV tube 9 would be connected to the small fluid regulation pump 21. The fluid regulation pump 21 would be hung from the other side of the double-sided "J"-shaped hook 2. The IV tube 9 would then be threaded through the tube-winding device 8 and adjusted to the desired length. The IV tube 9 would then be threaded through aperture 10 in side 29 of the carrying case 12 for attachment to an intravenous needle for insertion into a patient in an appropriate manner.

Telescoping pole 3 could be fully collapsed and the IV tubing 9 retracted so that a patient can carry the carrying case 12. Telescoping pole 3 could be fully extended and the IV tubing could be extended so that a patient can place the carrying case 12 on the ground or other stationary positions. In either the fully collapsed position, such as is depicted in FIG. 2, or in the fully extended position, such as is depicted in FIG. 1, the exemplary embodiment would be capable of delivering fluid intravenously.

If a patient that is connected to the exemplary embodiment for intravenous fluid delivery wanted to sit or stay in a stationary position, the patient would first open zipper 13 to open compartment 18. The patient would then reach into compartment 18 and press release button 30 on the tube-winding/retraction device 8 to allow release and extension of the IV tube 9. The patient could place the carrying case 12, for example, on the ground. In order to fully extend the telescoping pole 3, the patient would then press the spring-loaded button 1 to enable the compressed spring 23 to raise the telescoping pole 3 to its maximum height. When the telescoping pole 3 has reached its maximum height, spring loaded buttons 31, 32, and 33 would open through apertures 4, 5 and 6, respectively, in tubular members 25, 26, and 27, respectively, thereby locking the telescoping pole 3 in its fully extended position.

Depending on the particular medical fluid application, it may be possible to turn the pump 21 off when the telescoping pole 3 is fully extended—that is because some medical fluid delivery systems can work on the basis of gravity alone when the height of the medical fluid delivery bag 7 is sufficiently higher than the point of fluid delivery into the body of a patient.

Figure 5:
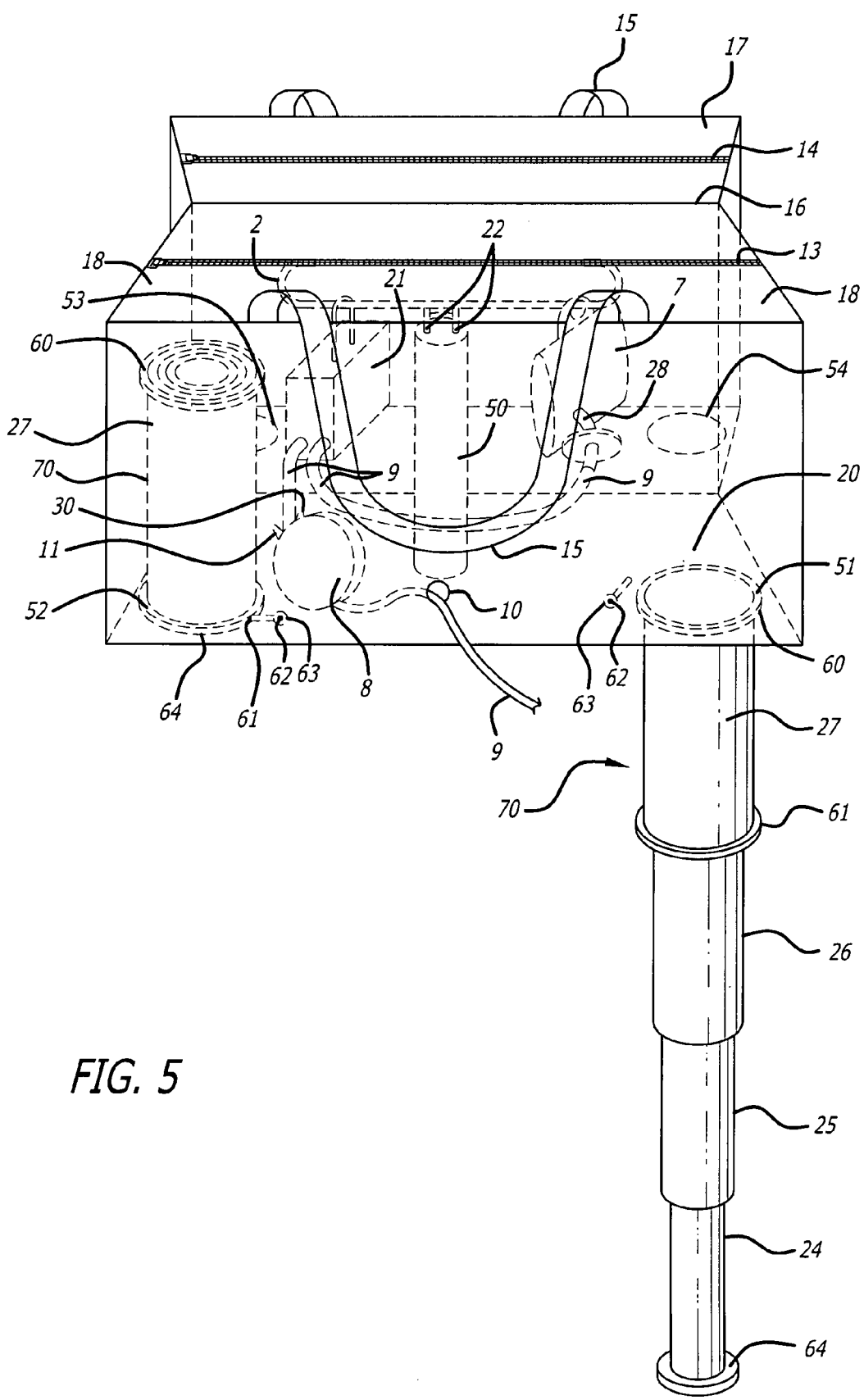
FIG. 5 is a perspective view of an alternative exemplary embodiment of the present invention.

FIG. 5 is a perspective view of an alternative exemplary embodiment of the present invention.

As depicted in FIG. 5, instead of using a telescoping pole 3 as was used in the exemplary embodiment (see FIG. 1) on which to mount an IV bag 7 and a fluid regulation pump 21, the alternative exemplary embodiment uses a stationary tubular member 50 on which to mount an IV bag 7 and a fluid regulation pump 21.

As depicted in FIG. 5, in the alternative exemplary embodiment, a double-sided "J" shaped hook 2 would be provided. In the alternative exemplary embodiment, the double-sided "J" shaped hook 2 would be made of a strong metal with a length of approximately 4 inches and would be affixed to the top of the stationary tubular member 50 by means of two vertical posts 22.

As depicted in FIG. 5, in the alternative exemplary embodiment, a tube-winding/retraction device 8 would be provided. As with the exemplary embodiment, in the alternative exemplary embodiment, the tube-winding device 8 would measure approximately 4 inches in diameter and approximately 1 inch wide.

In the alternative exemplary embodiment, four identical telescoping legs 70 (two telescoping legs 70 are depicted in FIG. 5—one fully expanded; one collapsed) would be provided. In the alternative exemplary embodiment, the telescoping legs 70 would be made out of a lightweight plastic or aluminum. In the alternative exemplary embodiment, a telescoping leg 70 would be inserted through each floor aperture 51, 52, 53, and 54 as depicted in FIG. 5 on the bottom 20 of the carrying case 12.

Each of the four telescoping legs 70 would comprise a plurality of tubular members, e.g., 27, 26, 25, and 24 as depicted in FIG. 5. That is, the telescoping legs 70 of the alternative exemplary embodiment, would be similar to the telescoping pole 3 of the exemplary embodiment, including spring-loaded buttons, e.g., 1, 31, 32, and 33 (not visible in FIG. 5), apertures, e.g., 4, 5, and 6 (not visible in FIG. 5), outwardly flared ridges, 24*a*, 25*a*, and 26*a* (not visible in FIG. 5), and inward detents 25*b*, 26*b*, and 27*b* (not visible in FIG. 5), to lock the legs 70 in their extended position and/or in their collapsed positions.

In the alternative exemplary embodiment, each telescoping leg 70 would be extended to raise carrying case 12 when such a raised position was preferred by the patient, such as when the patient wanted to remain in a stationary period for some time.

In the alternative exemplary embodiment, as depicted in FIG. 5, circular piece 64 would be provided. Circular piece 64 would be attached to the bottom of tubular member 24 of each telescoping leg 70. Circular piece 64 would be provided to increase the surface area between the carrying case 12 and the ground when the telescoping legs 70 are extended for more stability. In the alternative exemplary embodiment, circular piece 64 would have a rubber tread on the bottom so as to further stabilize the raised carrying case 12 and create a non-slip surface.

In the alternative exemplary embodiment, base tubular member 27 would be provided with an outwardly flared ridge 60 to prevent base tubular member from dislodging from its respective aperture 51, 52, 53, or 54 when the telescoping leg 70 is extended.

When the telescoping legs 70 are collapsed, such as the telescoping leg 70 pictured in aperture 52 in FIG. 5, base tubular member 27 slides inside compartment 18 of the carrying case 12. In the alternative exemplary embodiment, base tubular member 27 would be provided with an outwardly flared ridge 61 to prevent base tubular member from dislodging inside compartment 18 from its respective aperture 51, 52, 53, or 54 when the telescoping leg 70 is collapsed.

In the alternative exemplary embodiment, when each telescoping leg 70 is collapsed, the telescoping leg 70 will lock in its collapsed position, as was explained for telescoping pole 3 in the exemplary embodiment, with spring-loaded button 1 locking through apertures 4, 5 and 6.

Figure 6:
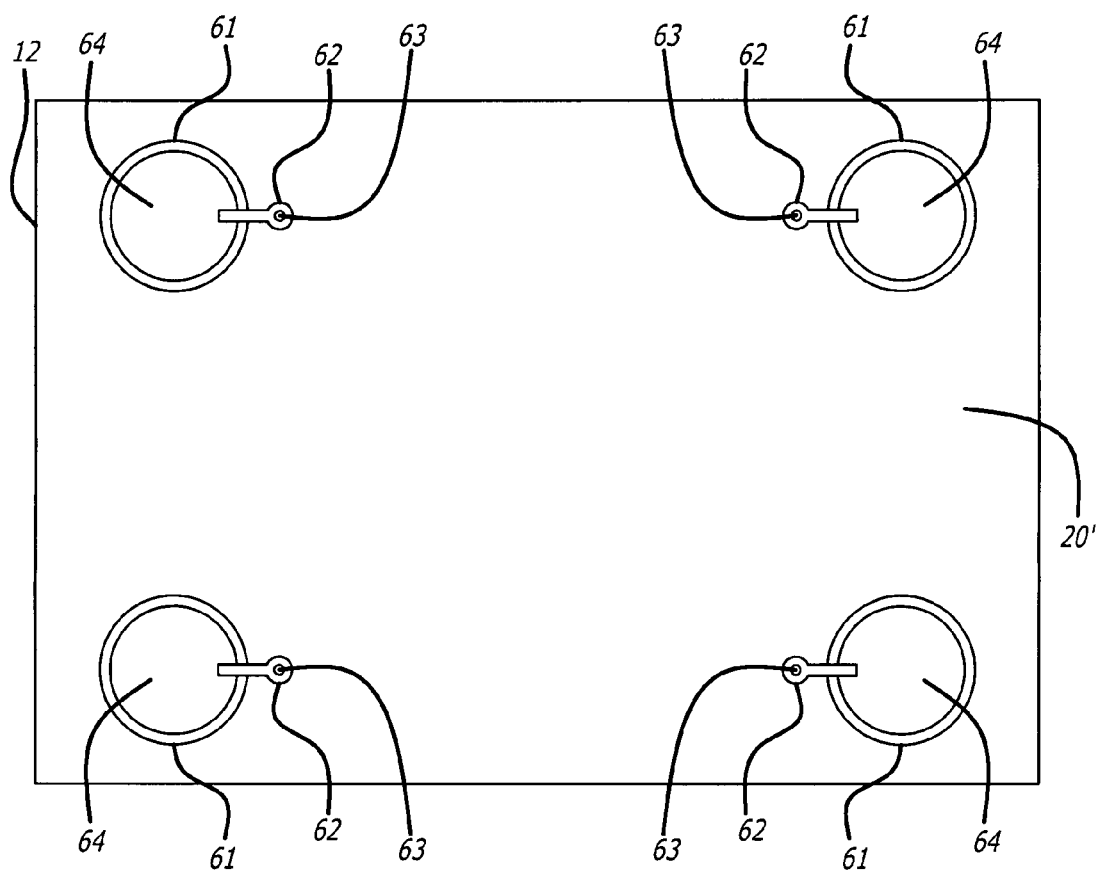
FIG. 6 is a bottom plan view of the bottom of an alternative exemplary embodiment of the present invention.

FIG. 6 is a bottom plan view of the exterior bottom 20' of the alternative exemplary embodiment of the present invention. In the alternative exemplary embodiment, a rotatable clip 62 would be fastened by a brad 63 to the exterior bottom 20' of the carrying case 12 near each telescoping leg 70. When a telescoping leg 70 is collapsed into compartment 18, the rotatable clip 62 nearest that telescoping leg 70 could be rotated so that the clip 62 covers a portion of the outwardly flared ridge 61, to prevent the base tubular member 27 from sliding out of the compartment 18. As will be understood by someone with ordinary skill in the art, alternative means other than a rotatable clip 62 fastened with a brad 63 for preventing the telescoping leg from sliding out the compartment 18 could be provided without departing from the spirit of the present invention.

As will be understood by someone with ordinary skill in the art, dimensions, materials, and component sizes other than those mentioned above in describing the exemplary and alternative exemplary embodiments could be used without varying from the spirit of the invention.

As will be understood by someone with ordinary skill in the art, other features and characteristics of the present invention are depicted or are implicit in the accompanying figures and above-provided description.

Facsimile Reproduction of Copyright Material

A portion of the disclosure of this patent document contains material which is subject to copyright protection by the copyright owner, Michelle Gaster, or her successors or assigns. The copyright owner has no objection to the facsimile reproduction by anyone of the patent document or the patent disclosure, as it appears in the Patent and Trademark Office patent file or records, but otherwise reserves all copyright rights whatsoever.

Illustrative Embodiments

Although this invention has been described in certain specific embodiments, many additional modifications and variations would be apparent to those skilled in the art. It is, therefore, to be understood that this invention may be practiced otherwise than as specifically described. Thus, the embodiments of the invention described herein should be considered in all respects as illustrative and not restrictive, the scope of the invention to be determined by the appended claims and their equivalents rather than the foregoing description.

What is claimed is:

1. A medical fluid administration device for delivering medical fluids to, or collecting medical fluids from, a patient while the device is in either a collapsed state or in an expanded state, said medical fluid administration device comprising:

a fluid container comprising a reservoir for storing fluid, the fluid container further comprising an opening to the reservoir for fluid transport in to, or out of, the reservoir, and the fluid container further comprising a suspension device receiving means for receiving a suspension device for suspending the fluid container;

a collapsible, telescoping pole comprising a base, a plurality of interconnected telescoping sub-poles, and a top, the collapsible telescoping pole configured for extending the collapsible, telescoping pole to a fully telescoped state and for collapsing the collapsible, telescoping pole to a fully collapsed state, wherein the top of the collapsible, telescoping pole comprises a fluid container suspension means for suspending the fluid container;

a medical fluid pump for regulating transport of fluids, the medical fluid pump comprising a fluid direction control means that is configurable for directing delivery of fluid to the fluid container and for directing transporting of fluid from the fluid container;

a first portion of medical fluid tubing for transporting medical fluids, the first portion of medical fluid tubing comprising a first end, and a second end, the first end of the first portion of medical fluid tubing being connected to the opening to the fluid container, and the second end of the first portion of medical fluid tubing being connected to the medical fluid pump;

a medical fluid tubing extension-retraction device, the tubing extension-retraction device comprising a fluid tubing engaging means for engaging medical fluid tubing for uninterrupted fluid transport, the tubing extension-retraction device further comprising a retraction means for retracting medical fluid tubing for uninterrupted fluid transport, the tubing extension-retraction device further comprising an extension means for extending medical fluid tubing for uninterrupted fluid transport;

a second portion of medical fluid tubing for transporting medical fluids, the second portion of medical fluid tubing comprising a first end, a second end, and a middle portion, the first end of the second portion of medical fluid tubing being connected to the medical fluid pump, the middle portion of the second portion of medical fluid tubing being wound as a coil around a portion of the medical fluid tubing extension-retraction device for uninterrupted fluid transport when the second portion of medical fluid tubing is in a fully retracted state, the second end of the second portion of medical fluid tubing extending from the tubing extension-retraction device for delivering fluids to, or receiving fluids from, a patient; and a carrying case, the carrying case comprising:
  a compartment for completely encasing the fluid container, the medical fluid pump, the first portion of medical fluid tubing, the second portion of medical fluid tubing, and the collapsible, telescoping pole when the collapsible, telescoping pole is in a completely collapsed state,
  an interior floor connected to the base of the collapsible, telescoping pole, and
  an aperture through which the second end of the second portion of medical fluid tubing extends.

2. The medical fluid administration device of claim 1, wherein the collapsible, telescoping pole is spring loaded.

3. The medical fluid administration device of claim 2, wherein the collapsible, telescoping pole comprises a base sub-pole, a top sub-pole, and a plurality of telescoping sub-poles, wherein the base sub-pole comprises an aperture, wherein each telescoping sub-pole comprises a spring-loaded button and an aperture, and wherein the top sub-pole comprises a spring-loaded button.

4. A medical fluid administration device carrying apparatus for administering delivery or collection of medical fluids while the medical fluid administration device is in either a collapsed state or in an expanded state, said apparatus comprising:
  a carrying case comprising a compartment, the compartment comprising an interior floor, the carrying case comprising a bottom and an exterior bottom;
  a plurality of collapsible, telescoping poles mounted to bottom of the carrying case, each collapsible telescoping pole of the plurality of collapsible, telescoping poles extendable to a fully telescoped state beyond the exterior bottom and each collapsible telescoping pole of the plurality of collapsible, telescoping poles collapsible to a fully collapsed state completely within the carrying case;
  a stationary pole mounted to the interior floor of the carrying case, said stationary pole comprising a means for suspending a medical fluid container;
  a portion of medical fluid tubing comprising a first end, a middle portion, and a second end, the second end being connected to the medical fluid container, and the first end comprising a fluid transport means for delivery of fluids to, or a receiving of fluids from, a patient;
  a tubing extension-retraction device, the tubing extension-retraction device comprising a tube engaging means for engaging the middle portion of the portion of medical fluid tubing, the tubing extension-retraction device comprising a retraction means for winding the middle portion of the portion of medical fluid tubing as a coil around a portion of the retraction means for retracting the second end of the portion of medical fluid tubing, the tubing extension-retraction device further comprising an extension means for unwinding the coil of the middle portion of the portion of medical fluid tubing in order to extend second end of the portion of medical fluid tubing, and
  the middle portion of the portion of medical fluid tubing is disposed in a coil around a portion of the tubing extension-retraction device for uninterrupted fluid transport.

5. An apparatus for concealed transport of a medical fluid administration device, said device capable of one of infusing medical fluids to, or collecting medical fluids from, a body of a patient during concealed transport, said apparatus comprising:
  a carrying case comprising an interior floor and a closable opening disposed in the top of the carrying case;
  a medical fluid container;
  a pump, the pump comprising a direction-reversing pumping means for pumping medical fluids in a direction selected from the group consisting of: 1) pumping medical fluids from the medical fluid container for delivery to the body of the patient, and 2) pumping medical fluids for collection from the body of the patient to the medical fluid container;
  a collapsible stand disposed within the carrying case, the collapsible stand comprising a base that is connected to the interior floor of the carrying case, the collapsible stand further comprising an extension means for extending the collapsible stand to a fully extended state beyond the closable opening of the carrying case during stationary use, the collapsible stand further comprising a collapsing means for collapsing the collapsible stand to a fully collapsed state completely within the carrying case, the collapsible stand further comprising a first suspending means for suspending the medical fluid container and a second suspending means for suspending the pump;
  a first portion of medical fluid tubing comprising a first end of the first portion, a middle portion of the first portion, and a second end of the first portion, the second end of the first portion being connected to the pump, and the first end of the first portion comprising a fluid transport means for delivering fluids to, or receiving fluids from, a patient;

a second portion of medical fluid tubing comprising a first end of the second portion and a second end of the second portion, the first end of the second portion being connected to the medical fluid container, and the second end of the second portion being connected to the pump;

a tube-winding device, the tube-winding device comprising a tube-engaging means for engaging the middle portion of the first portion of medical fluid tubing for uninterrupted fluid transport, the tube-winding device further comprising a winding means for winding the middle portion of the first portion of medical fluid tubing as a coil around a portion of the tube-winding device in order to retract the first end of the first portion of medical fluid tubing for uninterrupted fluid transport when the collapsible stand is collapsed within the carrying case, and further comprising an unwinding means for unwinding the coil of the middle portion of the first portion of medical fluid tubing in order to extend the first end of the first portion of medical fluid tubing for uninterrupted fluid transport when the collapsible stand is extended beyond the carrying case;

the middle portion of the first portion being disposed as a coil around the tube-engaging means for uninterrupted fluid transport when the first end of the first portion of medical fluid tubing is in a fully retracted state.

6. The apparatus of claim 5, wherein the tube-winding device further comprises a locking means for locking the first portion of medical fluid tubing in place.

7. The apparatus of claim 5 in which the pump is an intravenous fluid delivery pump.

8. The apparatus of claim 5 in which the pump is a gastrointestinal nourishment delivery pump.

9. The apparatus of claim 5 in which the pump is an insulin delivery pump.

10. The apparatus of claim 5 in which the pump is a urine collection pump.

11. The apparatus of claim 5 in which the pump is a colostomy collection pump.

12. An apparatus for concealed transport of a medical fluid administration device, wherein during concealed transport, said medical fluid administration device is capable of at least one of infusing medical fluids to, or collecting medical fluids from, a body of a patient, said apparatus comprising:

a carrying case comprising a bottom and a closable opening disposed in the top of the carrying case;

a pump;

a fluid container;

a means for transporting fluid between the pump and the fluid container;

a telescoping pole fastened within the carrying case to the bottom of the carrying case, the telescoping pole comprising a top, wherein the top of the telescoping pole comprises a suspension means for suspending the pump and the fluid container, the telescoping pole comprising a plurality of telescoping subpoles for being extended through the closable opening disposed in the top of the carrying case during stationary use, and for being collapsed within the carrying case during ambulatory use;

a portion of medical fluid tubing for uninterrupted transport of medical fluids, the portion of medical fluid tubing comprising a first end, a middle portion, and a second end, the second end being connected to the pump, and the first end comprising a fluid transport means for delivering fluids to, or receiving fluids from, a patient; and a tube-winding device, the tube-winding device comprising a tube-engaging means for engaging the middle portion of the portion of medical fluid tubing, the tube-winding device further comprising a winding means for winding the middle portion of the portion of medical fluid tubing as a coil around a portion of the tube-winding device in order to retract the first end of the portion of medical fluid tubing for uninterrupted fluid transport when the telescoping pole is being collapsed to dispose the top of the telescoping pole within the carrying case, and further comprising an unwinding means for unwinding the coil of the middle portion of the portion of medical fluid tubing in order to extend the first end of the portion of medical fluid tubing for uninterrupted fluid transport when the telescoping pole is being telescoped to extend the top of the telescoping pole beyond the carrying case;

wherein the middle portion of the portion of medical fluid tubing is disposed as a coil around the tube-engaging means for uninterrupted fluid transport when the telescoping pole is in a fully collapsed state, and wherein the coil of the middle portion of the portion of medical fluid tubing is at least partially unwound as the telescoping pole is at least partially telescoped to extend through the closable opening disposed in the top of the carrying case.

13. The apparatus of claim 12 in which the pump is an intravenous fluid delivery pump.

14. The apparatus of claim 12 in which the pump is a gastrointestinal nourishment delivery pump.

15. The apparatus of claim 12 in which the pump is an insulin pump.

16. The apparatus of claim 12 in which the pump is a urine collection pump.

17. The apparatus of claim 12 in which the pump is a colostomy collection pump.

18. The medical fluid administration device of claim 1, the fluid container suspension means comprising:

a horizontal bar attached at the top of the telescoping pole, the horizontal bar comprising a first end and a second end, the first end comprising an upward curvature adapted for engaging the suspension device receiving means of the fluid container, and the second end comprising an upward curvature adapted for engaging the suspension device receiving means of the fluid container.

* * * * *